United States Patent [19]

Fain

[11] Patent Number: 5,558,098
[45] Date of Patent: Sep. 24, 1996

[54] METHOD AND APPARATUS FOR DETECTING LEAD SENSING ARTIFACTS IN CARDIAC ELECTROGRAMS

[75] Inventor: Eric S. Fain, Menlo Park, Calif.

[73] Assignee: Ventritex, Inc., Sunnyvale, Calif.

[21] Appl. No.: 556,790

[22] Filed: Nov. 2, 1995

[51] Int. Cl.$^6$ .................................................. A61B 5/0402
[52] U.S. Cl. ............................... 128/706; 607/5; 128/901
[58] Field of Search ................................ 128/696, 702, 128/705, 706, 901; 607/5, 14, 27

[56] References Cited

U.S. PATENT DOCUMENTS

| 4,960,123 | 10/1990 | Maker. | |
|---|---|---|---|
| 5,366,486 | 11/1994 | Zipes et al. | 128/705 X |
| 5,366,487 | 11/1994 | Adams et al. | 607/5 |
| 5,370,125 | 12/1994 | Mason et al. | 128/705 |
| 5,486,199 | 1/1996 | Kim et al. | 607/5 |

FOREIGN PATENT DOCUMENTS

| 9209331 | 6/1992 | WIPO | 128/705 |
|---|---|---|---|
| 8304171 | 12/1993 | WIPO | 128/706 |

OTHER PUBLICATIONS

"Cardioverter Discharges Following Sensing of Electrical Artifact Due to Fluid Penetration in the Connector Port", Hief, et al., PACE, vol. 18, Aug. 1995, pp. 1589–1591.

*Primary Examiner*—William E. Kamm
*Assistant Examiner*—Jeffrey R. Jastrzab
*Attorney, Agent, or Firm*—Steven M. Mitchell; Mark J. Meltzer

[57] ABSTRACT

An ICD system and method for its use which will detect the presence of sensing artifacts caused by lead conductor fracture, lead insulation failure or connector port fluid penetration. When such a failure results in an incorrect detection of a tachyarrhythmia, the presence of sensing artifacts or noise is noted and charging of high voltage capacitors and/or delivery of high voltage therapy is avoided. The system of the invention includes at least two pairs of sensing electrodes which provide two distinct electrogram signals to the sensing and analysis circuitry of a pulse generator. Each signal is analyzed for heart rate. The rates are compared and if the rates detected are significantly different therapy is not delivered to the patient. The sensing electrode pairs may include four independent electrodes or there may be one electrode in common with each sensing pair. In an alternative embodiment, the two signals are compared by performing a correlation analysis.

15 Claims, 2 Drawing Sheets

METHOD AND APPARATUS FOR DETECTING LEAD SENSING ARTIFACTS IN CARDIAC ELECTROGRAMS

FIELD OF THE INVENTION

The present invention relates generally to implantable defibrillators and pacemakers and more particularly to a method and apparatus for detecting sensing artifacts or noise in cardiac electrograms, particularly sensing artifacts caused by lead conductor fracture, lead insulation failure or fluid penetration in a connector port.

BACKGROUND OF THE INVENTION

Implantable cardioverter defibrillator (ICD) systems are extremely reliable. However, the endocardial leads used in such systems tend to be the source of problems if they do occur. This is true because the leads are exposed to the hostile environment of the human body and are subjected to continuous flexure with each heart beat and crush at their introduction site. Further, the design requirement that the leads be as small in diameter as possible to fit through a vein results in a design which is somewhat vulnerable to mishandling. One of the most frequently used lead insulation materials is silicone rubber which has a tendency to propagate nicks or cuts. While polyurethane is less susceptible to cuts, it has shown a greater tendency to degrade with time. Both materials may fail when subjected to the phenomenon known as clavicular crush which is caused by pressure on the lead where it is positioned between the patient's clavicle and the underlying muscle. Another source of such problems is damage caused by sutures tied around leads for fixation of the leads. Thus, lead insulation failure has been one of the most frequent sources of problems with ICD systems, particularly with regard to the production of sensing artifacts.

In addition to problems with insulation, lead conductor fracture resulting in an intermittent make-break phenomenon can occur and can also cause sensing anomalies. This problem may typically result both from the constant flexing of the lead and clavicular crush mentioned above.

A further problem with sensing artifacts which has been identified results from fluid penetration in the connector port for the sensing conductor of an ICD. This can result in shorting between the two sensing conductors and sensing of artifacts by the ICD which are interpreted as ventricular fibrillation. See Hief et al., "Cardioverter Discharges Following Sensing of Electrical Artifact Due to Fluid Penetration in the Connector Port", PACE, August 1995, pp. 1589-1591.

A fracture in a lead conductor, a lead insulation failure which contacts one or more sensing conductors in the lead or fluid penetration in a connector port can cause artifacts to be sensed by the sensing and analysis circuitry of the pulse generator. These artifacts may contain frequencies which can be analyzed as tachycardia or fibrillation resulting in the initiation or delivery of one or more inappropriate high voltage shocks to the patient. It would be desirable to have an ICD system which is capable of determining whether a particular sensed electrogram is contaminated with sensing artifacts so that inappropriate shock delivery may be avoided.

It is thus an object of the invention to provide a method for determining whether an electrogram signal includes sensing artifacts caused by lead fracture, lead insulation failure or connector port fluid penetration.

It is another object of the invention to provide an ICD system which is capable of discriminating between an electrogram signal which includes sensing artifacts and one which does not.

SUMMARY OF THE INVENTION

The present invention provides an ICD system and method for its use which will detect the presence of sensing artifacts caused by lead fracture, lead insulation failure or connector port fluid penetration. When such sensing artifacts result in an incorrect detection of a tachyarrhythmia, the fact is noted and initiation or delivery of high voltage therapy is avoided. The system of the invention includes at least three sensing electrodes which provide two distinct electrogram signals to the sensing and analysis circuitry of the pulse generator. Each signal is analyzed for heart rate. If the rates detected are significantly different, one of the signals is probably contaminated with sensing artifacts from a lead fracture, lead insulation failure or connector port fluid penetration and high voltage therapy is not initiated or delivered to the patient. The difference may be a numerical difference in detected rate or may be based on one signal being in a tachyarrhythmia rate zone while the other signal is determined to be at sinus rate. The sensing electrodes may include four independent electrodes (i.e., two distinct pairs) or there may be one electrode in common with each sensing pair (i.e., three electrodes). For example, in a preferred embodiment, the primary sensing electrodes are the pacing/sensing electrode at the distal tip of a transvenous defibrillation lead and the right ventricular (RV) defibrillation electrode positioned on the lead proximal of the pacing/sensing electrode. The secondary sensing pair includes the RV defibrillation electrode and the metal housing of the pulse generator. Conductors for the pace/sense conductor electrode and RV defibrillation electrode are carried in the lead body. If there is a lead insulation failure which provides an electrical short path to the pace/sense conductor, noise may be detected as a tachycardia or fibrillation. Whenever such a determination is made by the sensing and analysis circuitry, the detected rate is compared to the rate determined for the secondary sensing pair. If the rates are substantially different or one signal is analyzed as a tachyarrhythmia and the other as sinus, then high voltage therapy will not be delivered. A warning flag will be placed in memory so that the next time the ICD is interrogated by the patient's physician the condition will be noted and the defective lead or ICD may be replaced. In another aspect of the invention, one or both of the electrograms are stored when therapy is avoided due to sensing artifact identification.

BRIEF DESCRIPTION OF THE DRAWING

The various features and advantages of the present invention may be more readily understood with reference to the following detailed description taken in conjunction with the accompanying drawings in which.

DETAILED DESCRIPTION OF THE INVENTION

Reference is made to copending patent application Ser. No. 219,605, filed Mar. 29, 1994 entitled "Method and Apparatus for Delivering Defibrillation Shocks With Improved Effectiveness" now U.S. Pat. No. 5,500,008 to the present inventor and assigned to the assignee of the present application, which application is incorporated herein by reference. In that application, a system is described wherein two separate sensing paths are used to determine the most effective time to deliver a defibrillation shock. The two sensing paths may or may not include a common electrode and conductor. For example, a bipolar signal sensor using the pacing/sensing electrode and defibrillation electrode for one sensing path and the defibrillation electrode to the defibrillator housing for the second sensing path to sense a unipolar or global signal.

For the invention to function properly, the electrode pairs for providing the electrogram signals must be chosen such that if the insulation of the primary sense conductor or the conductor itself is fractured or otherwise fails, a signal from the second pair of electrodes will not be contaminated by sensing artifacts or noise. Thus, in a preferred embodiment, the first pair of electrodes to provide a electrogram signal is that normally used for continuous sensing of cardiac function. This will typically be a bipolar sense pair placed at the distal end of a transvenous lead. In the preferred embodiment of the invention, the bipolar signal is provided between a distal pacing tip electrode and an RV defibrillation electrode. In such a configuration, the second sensing pair could be between the RV defibrillation electrode and the defibrillator housing; the distal pacing tip electrode and the defibrillator housing; or between the RV and SVC defibrillation electrodes. One conventional transvenous defibrillation lead design includes three conductors: a pacing/sensing tip, a pacing/sensing ring, and an RV defibrillation coil. Primary sensing is between the pacing/sensing tip and the pacing/sensing ring. Secondary sensing can be: defibrillation coil to housing; pacing/sensing tip to housing; pacing/sensing tip to coil; pacing/sensing ring to coil; or pacing/sensing ring to housing. A Superior Vena Cava (SVC) defibrillation electrode on a separate lead could also be used.

Figure 1:
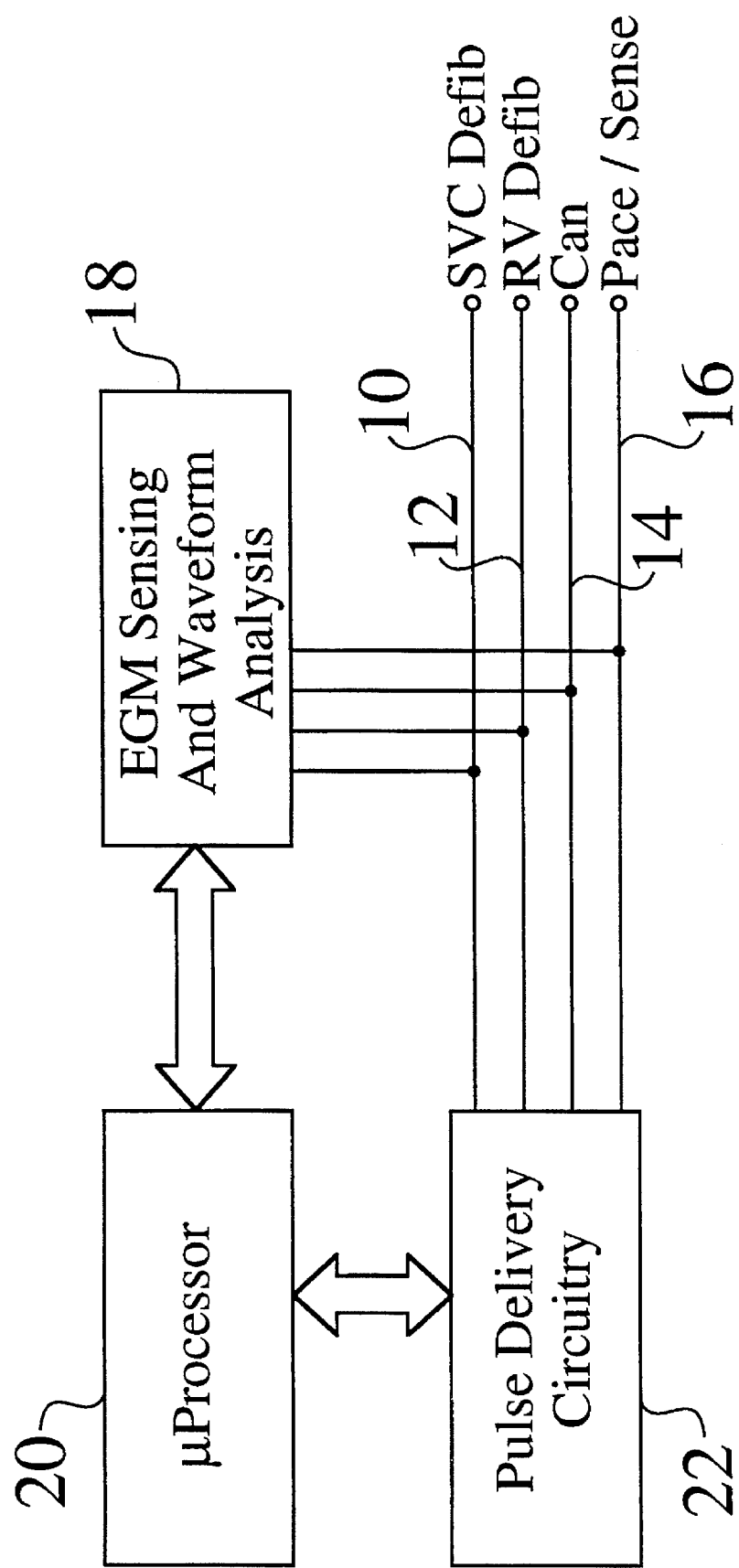
FIG. 1 is a schematic diagram of an implantable defibrillator system according to the invention.

The preferred embodiment of the invention will now be discussed with reference to FIG. 1 which provides a schematic diagram of an implantable defibrillator system according to the invention. Electrogram signals may be received along any pairs of electrode conductors including an SVC defibrillation conductor 10, an RV defibrillation conductor 12, a housing conductor 14 and a pace/sense conductor 16. The electrogram signals are received by electrogram sensing and waveform analysis circuitry 18. Such circuitry is well known in the art and is described in U.S. Pat. No. 5,014,701 to Pless et al, which patent is incorporated herein by reference. The sensing pairs to be used may be fixed or may be selectable with a switching matrix (not shown). The electrogram sensing and waveform analysis circuitry 18 communicates with and is controlled by a microprocessor 20. Electrical therapy may also be delivered along the conductors 10, 12, 14, 16 to their respective electrodes from pulse delivery circuitry 22. Such therapy typically includes Brady pacing, antitachycardia pacing, cardioversion and defibrillation.

Figure 2:
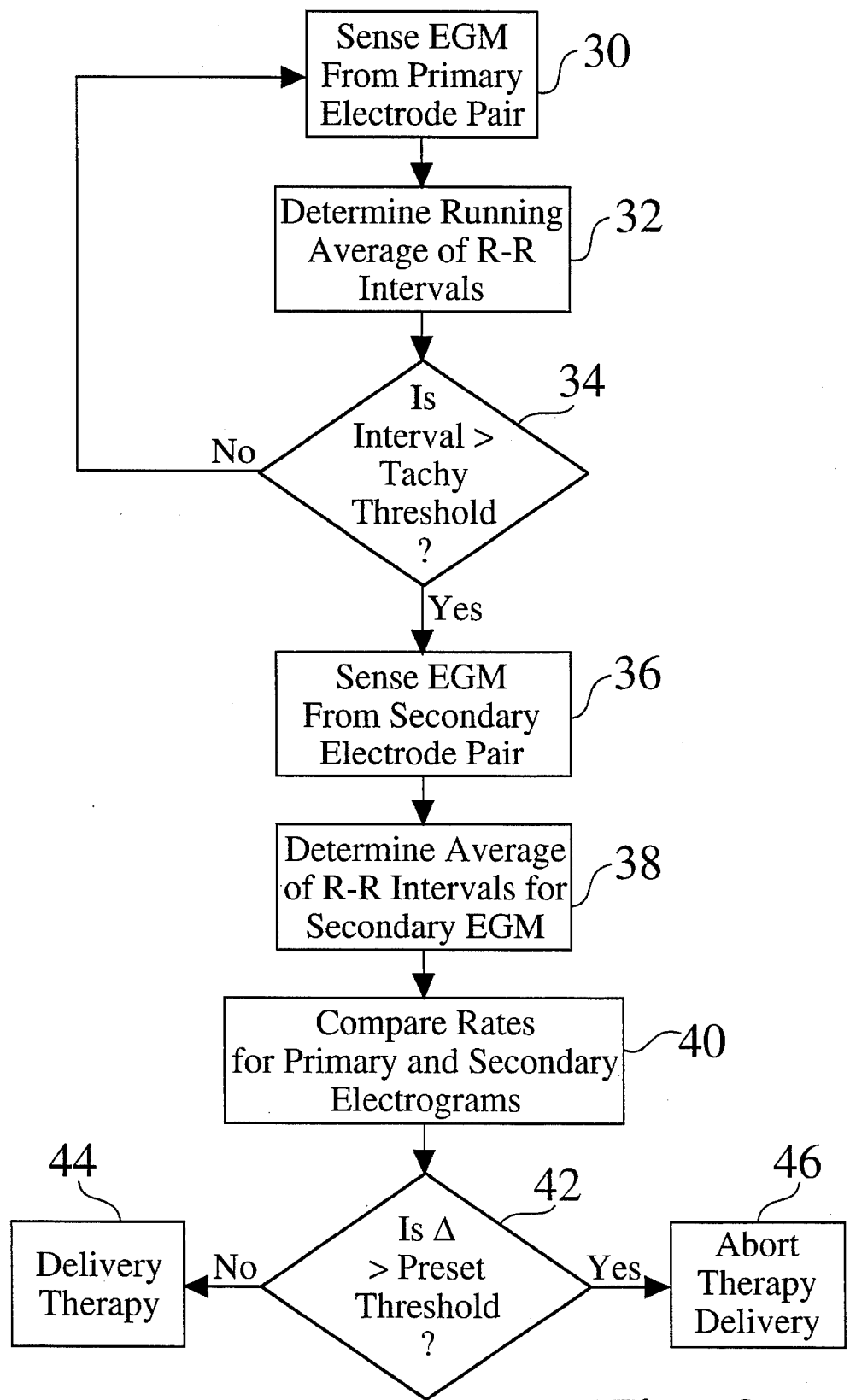
FIG. 2 is a flow chart of steps performed in practicing the method of the invention.

Operation of the apparatus and practice of the method of the invention will now be discussed with reference to FIGS. 1 and 2. FIG. 2 is a flow chart of steps performed in practicing the method of the invention. An electrogram is continuously sensed by electrogram sensing and waveform analysis circuitry 18 from a primary electrode pair in step 30. In a preferred embodiment, this signal is sensed between the pacing/sensing electrode coupled to conductor 16 and the RV defibrillation electrode coupled to conductor 12. The electrogram sensing and waveform analysis circuitry 18 continuously determines cardiac event intervals, R—R intervals typically, and a running average of the patient's heart rate at step 32. The detected heart rate is then compared to various tachycardia and fibrillation thresholds at step 34 to determine whether there may be a tachyarrhythmia present. The waveform may also be analyzed for other features such as waveform morphology for purposes of arrhythmia discrimination. If a tachyarrhythmia is not present, the algorithm continues with sensing the electrogram from the primary electrode pair at step 30. If, however, a tachyarrhythmia is detected at step 34, an electrogram from a secondary electrode pair is sensed at step 36. Charging of high voltage capacitors may be initiated upon determination of a tachyarrhythmia in the primary electrogram. It should be understood that electrograms from the secondary electrode pair could also be continuously sensed and a continuous comparison of the sensed heart rates or heart rhythm analysis could be made. In a preferred embodiment, the secondary electrogram signal is sensed between the RV defibrillation electrode coupled to conductor 12 and the housing or can electrode coupled to conductor 14. The electrogram sensing and waveform analysis circuitry 18 will then determines R—R intervals and an average of the patient's heart rate at step 38. The secondary electrode pair selected could alternatively be the pacing/sensing tip electrode coupled to conductor 16 and the can electrode coupled to conductor 14 or the RV and SVC defibrillation electrodes. The heart rates from steps 32 and 38 are compared at step 40. Various mathematical techniques could be used for the comparison but the simplest comparison is to take the difference between the two rates. A determination is then made at step 42 if the difference exceeds some preset threshold. This threshold can be set relatively small such as for example 10 beats per minute since the two electrograms should be providing substantially the same rate unless there are sensing artifacts or noise in one of the sensed signals. If the difference is less than the threshold, then therapy is delivered at step 44. However, if the rate difference exceeds the threshold, then there is an indication of noise or artifacts caused by a lead insulation fracture or failure and therapy is aborted at step 46. Aborting therapy includes termination of charging of the high voltage capacitors where that was initiated upon initial tachyarrhythmia detection or prevention of device charging initiation.

In an alternative embodiment, steps 32 and 38 assign a rhythm analysis to each interval, i.e., sinus, slow tachycardia, fast tachycardia or fibrillation. The comparison at step 40 is whether the secondary electrode pair also senses a non-sinus rate. Thus, if a tachyarrhythmia is detected in each electrogram, a therapy is delivered at step 44. If, however, a sinus rate is determined in the secondary electrogram, therapy is aborted at step 46.

In another alternative embodiment of the invention, a correlation analysis can be performed to compare the two electrogram signals. In this regard, reference is made to copending patent application Ser. No. 343,294, filed Nov. 22, 1994 entitled "Correlator based Electromagnetic Interference Responsive Control System Useful in Medical Devices" to Mark Meltzer and assigned to the assignee of the present application, which application is incorporated herein by reference. Basically, if the signals exhibit a high degree of correlation then there are probably no substantial sensing artifacts and therapy should be delivered in response to a detected tachyarrhythmia. On the other hand, if there is a lower level of correlation, this is indicative of sensing artifacts and therapy should not be delivered.

In a further alternative embodiment of the invention, sensing is performed with a dedicated bipolar sensing pair.

In this case, two separate sensing electrodes are positioned at the distal end of a transvenous lead, each connected to a proximal connector with a separate conductor. The proximal connector has a separate lead terminal for each conductor. If fluid leaks into the connector port area, it may cause a short between the sensing electrode pair. A secondary electrode pair will not be affected by the fluid intrusion and will not exhibit false tachyarrhythmia detection from the sensed artifacts. In this alternative embodiment it is preferable that the secondary sensing pair not have a common electrode and conductor with the primary sensing pair. Thus, the secondary sensing pair can be the RV defibrillation electrode and the pulse generator housing. This configuration of separate primary and secondary sensing pairs is also desirable in the case of a conductor fracture with intermittent make-break phenomenon producing sensing artifacts. In the event of a conductor fracture in the primary pair, the secondary pair cannot be using the fractured conductor for sensing as might be the case where the secondary sensing pair has a common electrode/conductor with the primary pair.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A method for detecting the presence of sensing artifacts in a sensed cardiac electrogram comprising the steps of:

sensing a first electrogram signal from a first pair of electrodes;

sensing a second electrogram signal from a second pair of electrodes;

analyzing each of said first and second electrogram signals for cardiac event interval information; and comparing said event interval information for said first electrogram signal with said event interval information for said second electrogram signal to determine if sensing artifacts are present in one of said electrogram signals.

2. The method of claim 1 wherein said step of analyzing comprises determining a heart rate for each sensed electrogram signal.

3. The method of claim 2 wherein said step of comparing includes the step of determining whether said determined heart rates are within a predetermined range of each other.

4. The method of claim 2 wherein said step of comparing includes the step of determining whether said determined heart rates are both above a tachyarrhythmia rate threshold.

5. The method of claim 1 and further including the step of aborting a high voltage therapy delivery if the presence of sensing artifacts is detected in one of said electrograms.

6. The method of claim 5 and further including the steps of initiating charging of high voltage capacitors upon detection of a tachyarrhythmia in said first electrogram signal and halting charging if the presence of sensing artifacts is detected in one of said electrograms prior to delivery of said high voltage therapy.

7. The method of claim 1 and further including the step of recording in a memory a determination that sensing artifacts were present in one of said electrogram signals.

8. The method of claim 1 and further including the step of recording in a memory at least one of said electrogram signals.

9. The method of claim 1 and further including the step of preventing initiation of high voltage capacitor charging if the presence of sensing artifacts is detected in one of said electrograms.

10. An apparatus for detecting the presence of sensing artifacts in a sensed cardiac electrogram comprising:

a first pair of electrodes for sensing a first electrogram signal;

a second pair of electrodes for sensing a second electrogram signal;

electrogram sensing and waveform analysis circuitry coupled to said first and second electrode pairs for analyzing each of said first and second electrogram signals for cardiac event interval information; and a processor for comparing said event interval information for said first electrogram signal with said event interval information for said second electrogram signal to determine if sensing artifacts are present in one of said electrogram signals.

11. The apparatus of claim 10 wherein said apparatus includes an implantable cardioverter defibrillator and a transvenous lead system.

12. The apparatus of claim 11 wherein said transvenous lead system includes a pacing/sensing electrode and an RV defibrillation electrode as said first electrode pair and said RV defibrillation electrode and a defibrillator housing as a second electrode pair.

13. The apparatus of claim 11 wherein said transvenous lead system includes a pacing/sensing tip electrode and a pacing/sensing ring electrode as said first electrode pair and an RV defibrillation electrode and a defibrillator housing as a second electrode pair.

14. A method for detecting the presence of sensing artifacts in a sensed cardiac electrogram comprising the steps of:

sensing a first electrogram signal from a first pair of electrodes;

sensing a second electrogram signal from a second pair of electrodes; and performing a correlation analysis of said first and second electrogram signals to determine if sensing artifacts are present in one of said electrogram signals.

15. A method for detecting the presence of sensing artifacts in a sensed cardiac electrogram comprising the steps of:

sensing a first electrogram signal from a first pair of electrodes;

sensing a second electrogram signal from a second pair of electrodes;

analyzing said first electrogram signal for cardiac event interval information and assigning each interval to one of a plurality of rate ranges including at least a sinus rate range and at least one tachyarrhythmia rate range; and when an interval of said first electrogram signal falls within one of said at least one tachyarrhythmia rate ranges determining if a corresponding one of said intervals for said second electrogram signal falls within said sinus range to determine if sensing artifacts are present in said first electrogram signal.

* * * * *